United States Patent
Iwata et al.

(10) Patent No.: US 6,879,180 B2
(45) Date of Patent: Apr. 12, 2005

(54) DISPLAY PANEL INSPECTION APPARATUS AND INSPECTION METHOD

(75) Inventors: Toshiaki Iwata, Tokyo (JP); Hitoshi Sakamoto, Tokyo (JP)

(73) Assignee: Tokyo Electronics Industry Co., Ltd., Tokyo (JP)

( * ) Notice: Subject to any disclaimer, the term of this patent is extended or adjusted under 35 U.S.C. 154(b) by 0 days.

(21) Appl. No.: 10/682,508

(22) Filed: Oct. 10, 2003

(65) Prior Publication Data

US 2004/0263202 A1 Dec. 30, 2004

(30) Foreign Application Priority Data

Jun. 27, 2003 (JP) ........................................ 2003-184427

(51) Int. Cl.[7] .......................... G01R 31/00; G01R 31/02
(52) U.S. Cl. ........................................ 324/770; 324/754
(58) Field of Search ................................ 324/754–758, 324/770

(56) References Cited

U.S. PATENT DOCUMENTS 5,691,764 A * 11/1997 Takekoshi et al. ............. 348/86
5,825,500 A * 10/1998 Iino et al. .................... 356/394

FOREIGN PATENT DOCUMENTS

| JP | 8-189946 | | 1/1995 |
| JP | 08-189946 | * | 7/1996 |
| JP | 11-183864 | | 12/1997 |
| JP | 11-014957 | * | 1/1999 |
| JP | 2000-147044 | * | 5/2000 |
| JP | 2000-321545 | * | 11/2000 |

* cited by examiner

*Primary Examiner*—David Zarneke
*Assistant Examiner*—Emily Y Chan
(74) *Attorney, Agent, or Firm*—Reed Smith LLP; Stanley P. Fisher, Esq.; Juan Carlos A. Marquez, Esq.

(57) ABSTRACT

A rotary base having first and second surfaces on which display panels are to be placed, and a rotation shaft. The first and second surfaces can be switched between a front position (facing position) and a top position facing upward. A fixture base supports the rotary base to be rotatable about the rotation shaft. A Z-axis drive mechanism moves the fixture base forward to a predetermined position and backward to be retreated from the predetermined position. When the fixture base is moved to the predetermined position by the Z-axis drive mechanism, a probe unit is connected to the display panel.

6 Claims, 8 Drawing Sheets

DISPLAY PANEL INSPECTION APPARATUS AND INSPECTION METHOD

CROSS-REFERENCE TO RELATED APPLICATIONS

This application is based upon and claims the benefit of priority from the prior Japanese Patent Application No. 2003-184427, filed Jun. 27, 2003, the entire contents of which are incorporated herein by reference.

BACKGROUND OF THE INVENTION

1. Field of the Invention

The present invention relates to a display panel inspection apparatus and inspection method for inspecting a thin display panel formed of, for example, liquid crystal elements, organic EL (electric luminescence) elements, plasma display elements and FEDs (field emission devices).

2. Description of the Related Art

Inspection of a liquid crystal panel or the like requires a time for mounting the liquid crystal panel on an inspection table of an inspection apparatus, a time for positioning the mounted liquid crystal panel with respect to a probe unit, a time for inspection, and a time for removing the liquid crystal panel from the inspection table after the inspection is completed. Therefore, the conventional inspection apparatus is large in scale and costs high.

Since the conventional inspection apparatus is large and expensive, there is a demand for compact and inexpensive inspection apparatus. It is expected that the reduction in cost of the inspection apparatus will lead to reduction in manufacturing cost of the liquid crystal panel itself.

BRIEF SUMMARY OF THE INVENTION

Accordingly, an object of the present invention is to provide a display panel inspection apparatus, which occupies a small space, has a simple structure and costs low, and also to provide an inspection method using the apparatus.

According to an aspect of the present invention, there is provided a display panel inspection apparatus comprising: a rotary base having first and second surfaces on which display panels are to be placed, and a rotation shaft inclined with respect to a horizontal so that the first and second surfaces can be switched between a front position (facing position) facing a front of the display panel inspection apparatus and a top position facing upward; a fixture base having a driving section which rotates the rotation shaft, and supporting the rotary base to be rotatable about the rotation shaft; a Z-axis drive mechanism which moves the fixture base toward the front of the display panel inspection apparatus to a predetermined position and backward to be retreated from the predetermined position; and a probe unit which faces to the surface of the rotary base that is at the front position (facing position) when the fixture base is moved to the predetermined position by the Z-axis drive mechanism.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general descriptions given above and the detailed descriptions of the preferred embodiments given below, serve to explain the principles of the invention.

DETAILED DESCRIPTION OF THE INVENTION

Embodiments of the present invention will be described with reference to the accompanying drawings. In this specification, the components common to the drawings are identified by the same reference symbols and a repetitive explanation is omitted.

Figure 1:
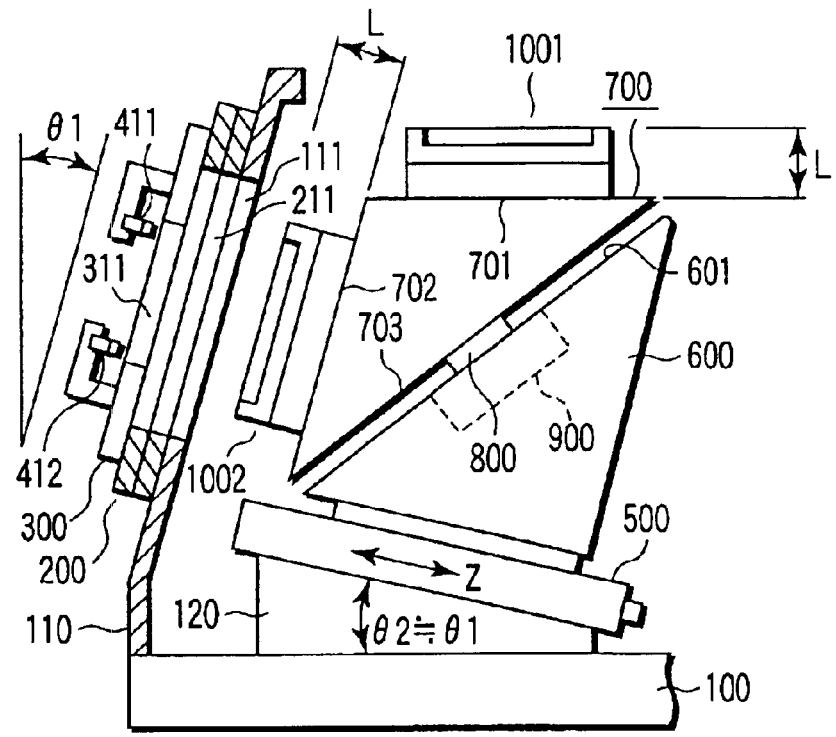
FIG. 1 is an explanatory diagram showing the structure of an apparatus according to an embodiment of the present invention.

FIG. 1 shows a side view of the basic structure of an inspection apparatus according to the present invention. The inspection apparatus is supported by a flat base 100. A front panel 110 stands up from a front edge of the base 100, and extends upward at an inclination angle θ1. A window 111 is formed in the front panel 110. A stage device 200 is attached to surround the window 111. The stage device 200 also has a window 211 corresponding to the window 111. A probe unit 300 is attached to surround the window 211. The probe unit 300 also has a window 311 corresponding to the windows 111 and 211. Therefore, an inspector can observe the inside of the front panel 110 through the windows 311, 211 and 111. As described above, in this system, the stage device 200 and the probe unit 300 are, for example, frame-shaped. The probe unit 300, attached to the stage device 200, is not necessarily frame-shaped, but may be columnar.

Video cameras 411 and 412 for positioning (alignment) are attached to the probe unit 300 via camera supporting sections to take images inside the apparatus through the windows 311, 211 and 111. Though FIG. 1 shows the two video cameras 411 and 412, the number of the video cameras is not limited to two. Further, the camera supporting sections need not be attached to the probe unit 300, but may be attached to the front panel.

The stage device 200 can adjust the position of the probe unit 300 in the directions of X-, Y- and θ-(rotation) axes. The X- and Y-axes are perpendicular to each other. A Z-axis, perpendicular to the X- and Y-axes will be described later. The symbol θ represents an angle of rotation about the Z-axis.

A support base 120 is fixed to the upper surface of the base 100. The upper surface of the support base 120 is inclined at an angle θ2 equal to θ1 with respect to the horizontal (the state in which θ2 is substantially equal to θ1 also falls under the scope of the present invention). A Z-axis drive mechanism 500, serving as a stage device, is attached to the upper surface of the support base 120. The Z-axis drive mechanism 500 supports a fixture base 600, and is capable of moving the fixture base 600 forward and backward (in the Z-axis directions). The fixture base 600 supports a rotary base 700 so as to be freely rotatable (or 180° reciprocatively rotatable).

The rotary base 700 has a first surface 701 and a second surface 702. A display panel can be mounted on each of the surfaces. The rotation axis of the rotary base 700 is inclined at an angle with respect to the horizontal, so that the first and second surfaces 701 and 702 can be switched between a front position (facing position) facing frontward and a top position facing upward. In the state shown in FIG. 1, the second surface 702 is located at the front position (facing position) and the first surface 701 is located at the top position (panel exchanging position). The front position can be called a facing position, because the display panel at this position faces the outside of the apparatus through the windows. The top position can be called a panel exchanging position, because the display panel at this position can be exchanged with another panel by a robot, as will be described later.

The rotary base 700 has a substantially triangular cross section having first, second and third sides in the side view. The first and second sides are sides of the first and second surfaces 701 and 702, on which display panels are to be placed. The third side is a side of a third surface 703, which is a rotation surface. A rotation shaft 800 is set in a substantially central portion of the third surface 703 and perpendicular to this surface.

The fixture base 600 has an opposing surface 601 opposing to the third surface 703. A motor 900, serving as driving means, is attached to a wall including the opposing surface 601. The shaft of the motor 900 is rotated or reciprocatively rotated under the control of a control unit (not shown). The motor 900 rotates the rotary base 700 via the rotation shaft 800.

Pallet devices 1001 and 1002 are attached to the first and second surfaces 701 and 702. The pallet devices 1001 and 1002 can hold display panels by suction means.

Figure 2:
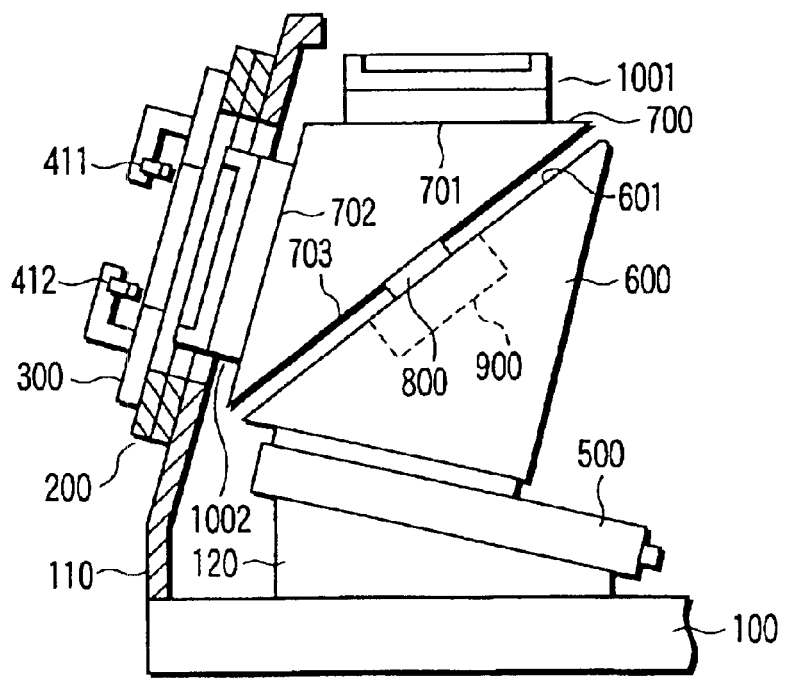
FIG. 2 is an explanatory diagram showing an operation state of the apparatus of the embodiment.

FIG. 1 shows a state in which the fixture base 600 has been moved back by the Z-axis drive mechanism 500. FIG. 2 shows a state in which the fixture base 600 has been moved forward by the Z-axis drive mechanism 500. When the fixture base 600 is located at a front predetermined position, the probe unit 300 faces one surface of the rotary base 700 in close proximity. In this position, therefore, probes of the probe unit 300 are brought into contact with terminal electrodes of the display panel mounted on the upper surface of the pallet device 1002. At this time, the probe unit 300 supplies power, a signal, an inspection voltage, an inspection current, etc., to the display panel, so that it can detect whether the display panel is normal or not.

To bring the probes of the probe unit 300 accurately in contact with the terminal electrodes of the display panel, the stage device 200 and the video cameras 411 and 412 play important roles, as described below. When the fixture base 600 and the rotary base 700 are moved forward by the Z-axis drive mechanism 500 and reach before the predetermined position, a control section (not shown) captures the image information taken by the video cameras 411 and 412 and determines whether a mark of the display panel falls within a preset area. If the mark of the display panel does not fall within the preset area, the stage device 200 is controlled so that the mark is positioned within the predetermined area. Then, the Z-axis drive mechanism 500 is controlled to move the display panel forward. As a result, the terminal electrodes of the display panel are accurately in contact with and electrically connected to the corresponding probes of the probe unit 300. In this state, the display panel can be subjected to various tests. If the video cameras cannot detect the mark of a display panel, the control section determines that no display panel is mounted, and displays an alarm and/or outputs and an alarm sound.

Figure 3:
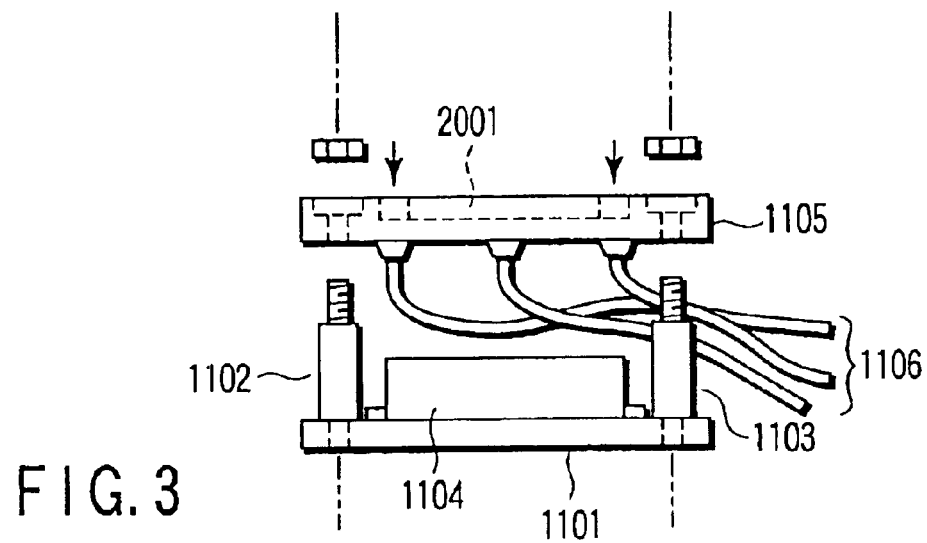
FIG. 3 is a diagram showing the structure of an example of the pallet device shown in FIG. 1.

FIG. 3 is a diagram for explaining the structure of the pallet device 1001. The pallet device 1002 has the same structure; therefore, only the pallet device 1001 is described as a representative. A plurality of support shafts 1102 and 1103 stand up in corner portions on the upper surface of a substrate 1101. A backlight unit 1104 is attached to the central portion of the upper surface of the substrate 1101. The support shafts 1102 and 1103 support a pallet 1105 made of, for example, a transparent plastic plate. The pallet 110S is also frame-shaped and has a window in its central portion. A display panel 2001 can be fitted to the window. To make the structure easily understandable, FIG. 3 shows a state in which the pallet 1105 is separated from the support shafts 1102 and 1103. When the apparatus is used, the pallet 1105 is attached to the support shafts 1102 and 1103. The periphery of the display panel 2001 can be fitted to L-shaped cut portions formed in peripheral portions of the frame of the pallet 1105. The cut portions have grooves, to which vacuum tubes 1106 are connected. The pallet of the present invention is not limited to the structure described above, but can be modified variously. The modifications will be described later.

With the above structure, the periphery of the display panel 2001 is attracted to sucking portions in the peripheral portions of the frame of the pallet 1105. As a result, the display panel 2001 is held by the pallet 1105.

According to the above description, the pallet device has a backlight. However, if the display panel to be inspected is formed of self-luminous elements (organic EL (electric luminescence) elements, plasma display elements and FEDs (field emission devices), or the like), it is unnecessary to use the backlight.

Figure 4:
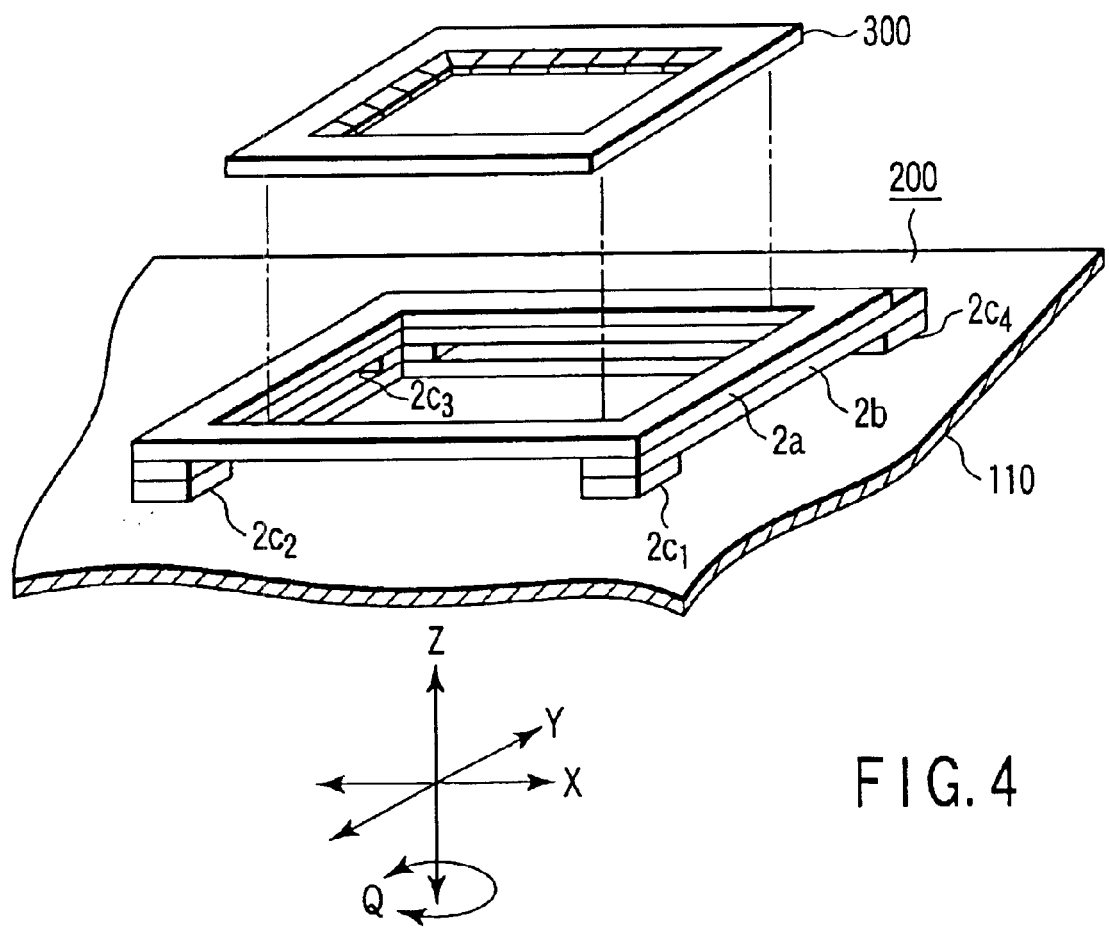
FIG. 4 is a diagram for explaining the structures of examples of the stage device and the probe unit shown in FIG. 1.

FIG. 4 shows basic structures of the stage device 200 and the probe unit 300. The probe unit 300 is fixed to the upper surface of the stage device 200. The stage device 200 can make fine adjustment of the probe unit 300 in the X-axis and Y-axis directions and the θ direction (see the arrows in the figure). The stage apparatus 200 can be embodied variously. In the present embodiment, small motors are attached to lower portions of corners of a plurality of stage plates. For example, an X- and Y-axis drive motor is arranged between the first and second stage plates 2a and 2b, so that the upper stage plate 2a can be adjusted exactly in the X-axis and Y-axis directions.

Further, small motors are attached to corner support plates 2c1 to 2c4 supporting the four corner portions of the stage plate 2b, so that the stage plate 2b can be rotated in the θ direction.

As described before, the apparatus of this invention has a characteristic structure having the fixture base 600 and the rotary base 700, wherein the rotary base 700 is rotated, so that the display panel to be inspected can face the probe unit 300. While the probe unit 300 is inspecting the display panel, the display panel located in the top position can be exchanged with another display panel to be inspected next.

Figure 5:
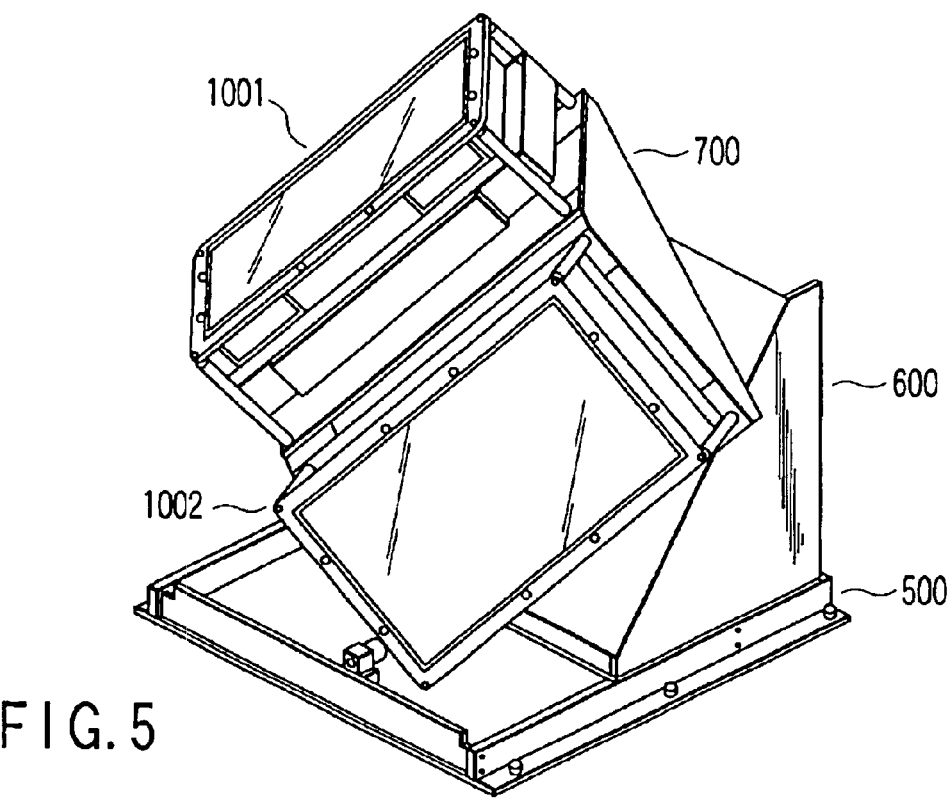
FIG. 5 is an explanatory diagram showing an operation state of the apparatus of the embodiment.
Figure 6:
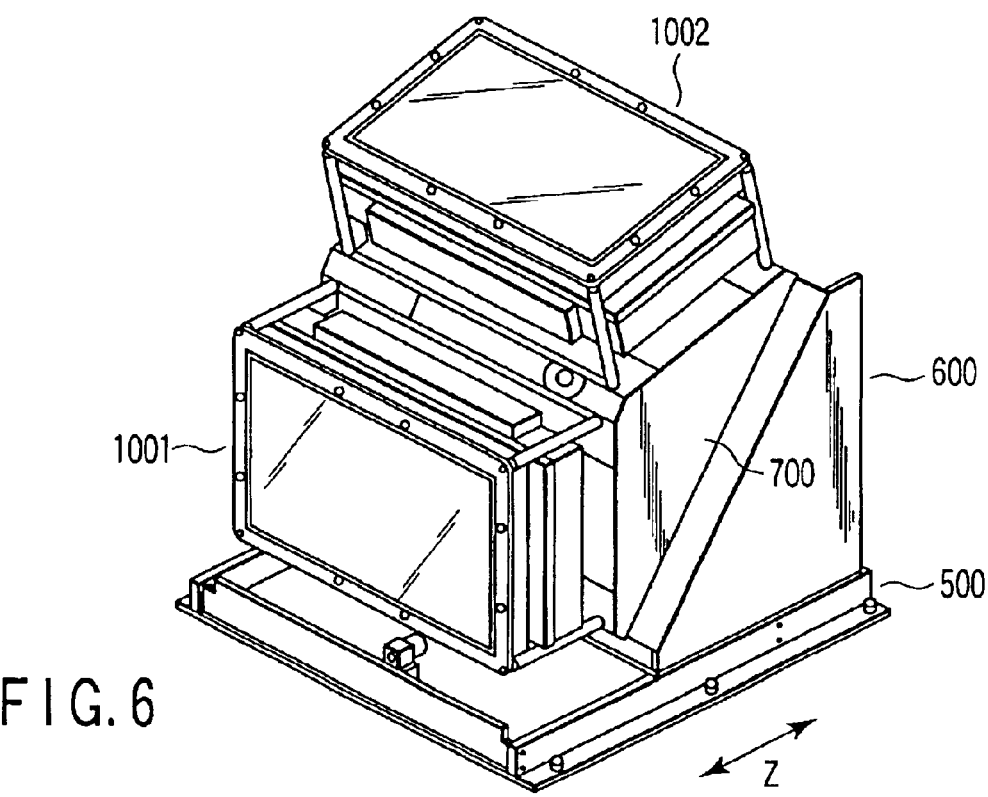
FIG. 6 is an explanatory diagram showing the apparatus of the embodiment, from which the front panel is removed.

FIG. 5 shows a state in which the rotary base 700 is rotating. FIG. 6 shows a state in which the rotary base 700 has been rotated. Thus, in the present invention, the rotary base 700 is rotated, so that the display panel to be inspected can face the probe unit 300. With this structure, the inspection apparatus occupies much smaller space as compared to the conventional apparatus. In addition, the structure of the apparatus itself is simple. Consequently, the apparatus costs low, which is effective in reducing the manufacturing cost of display panels.

Figure 7:
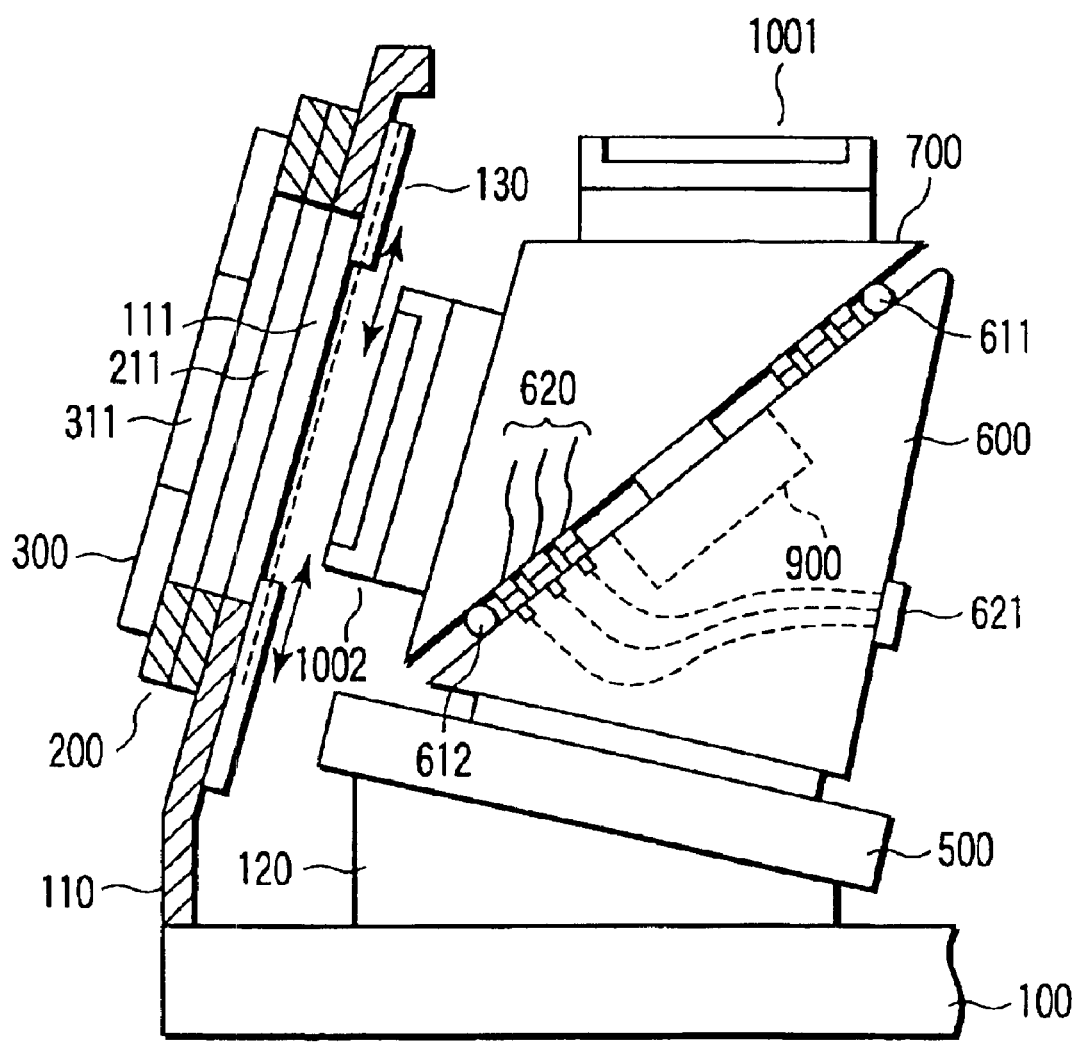
FIG. 7 is an explanatory diagram showing the structure of an apparatus according to another embodiment of the present invention.

The devices provided in the apparatus of the present invention and the functions thereof will be described in more detail with reference to FIG. 7. Ball bearings 611 and 612 may be interposed between the opposing surfaces of the rotary base 700 and the fixture base 600 in order to smoothen and stabilize the rotation of the rotary base 700. On the rotary base 700 having the pallet devices 1001 and 1002, it is necessary to operate the suction mechanism, the backlight, etc. For this purpose, a slip ring mechanism 620 is provided, which can electrically connect the opposing surfaces of the rotary base 700 and the fixture base 600. The slip ring mechanism 620 is connected to a system control section (not shown) through a connector 621. The slip ring mechanism 620 has a power source line and a control signal line to supply power and control the operations. FIG. 7 shows three slip rings, but more may be provided to control the operations other than the suction and backlight.

The pallet device 1001 is illuminated with backlight when faces forward. The operator, who carries out inspection through the windows 311, 211 and 111, may be dazzled by the backlight. Therefore, the window 111 may be kept shut by a shutter mechanism 130, until the rotary base 700 comes to the proper position.

The apparatus of the present invention is also characterized in that an alignment stage device is divided in two. In the conventional apparatus, a stage device for positioning needs a mechanism for adjustment in the X, Y and θ directions and a mechanism for adjustment in the Z direction. In the apparatus of the present invention, the Z-axis drive mechanism 500 for adjustment in the Z direction independently drives the fixture base 600. The mechanism for adjustment in the X-axis and Y-axis directions and the θ direction is mounted on the side of the front panel 110 (the stage device 200). Therefore, the mechanism on the side of the front panel 110 is simple and protrudes little. In particular, since the inspector faces the front panel, movement of the front panel in the Z-axis direction should preferably be avoided. Since the stage device 200 provided on the front panel 110 does not need a mechanism for adjustment in the Z-axis direction, the stage device 200 itself can be thin. It means that the height L (see FIG. 1) of the pallet devices 1001 and 1002 can be thin. In short, since the fixture base moves in the Z-axis directions, the stage device 200 and the pallet devices can be thin. It follows that the strokes in the Z-axis direction can be less. Furthermore, since the pallet devices can be thin, the distance between the backlight and the panel can be short. Consequently, the light emitted from the backlight can be effectively utilized.

The apparatus of the present invention is also characterized in that, in the posture in which the rotary base 700 is rotated to the predetermined position (inspection and display panel exchange posture), the top surface of the rotary base 700 is horizontal while the front surface facing forward is is inclined. The horizontal state of the top surface is convenient for exchanging of the display panels. The inclined state of the display panel on the front surface is convenient for the inspector.

The rotary base 700 may be of the type rotated in one direction (unidirectional rotation type) or 180° reciprocatively rotated (reciprocating rotation type), when the display panels are to be exchanged. In the case of 180° reciprocating rotation type, the fixture base 600 and the rotary base 700 can be electrically connected by a cable. In the case of unidirectional rotation type, slip rings are required.

In the apparatus of the present invention, as shown in FIG. 1, the angle θ2 of the Z-axis drive mechanism with respect to the horizontal is substantially the same as the angle θ1 of the inclination of the window for inspection. This setting also contributes to the horizontal state of the top surface of the rotary base 700.

Figure 8:
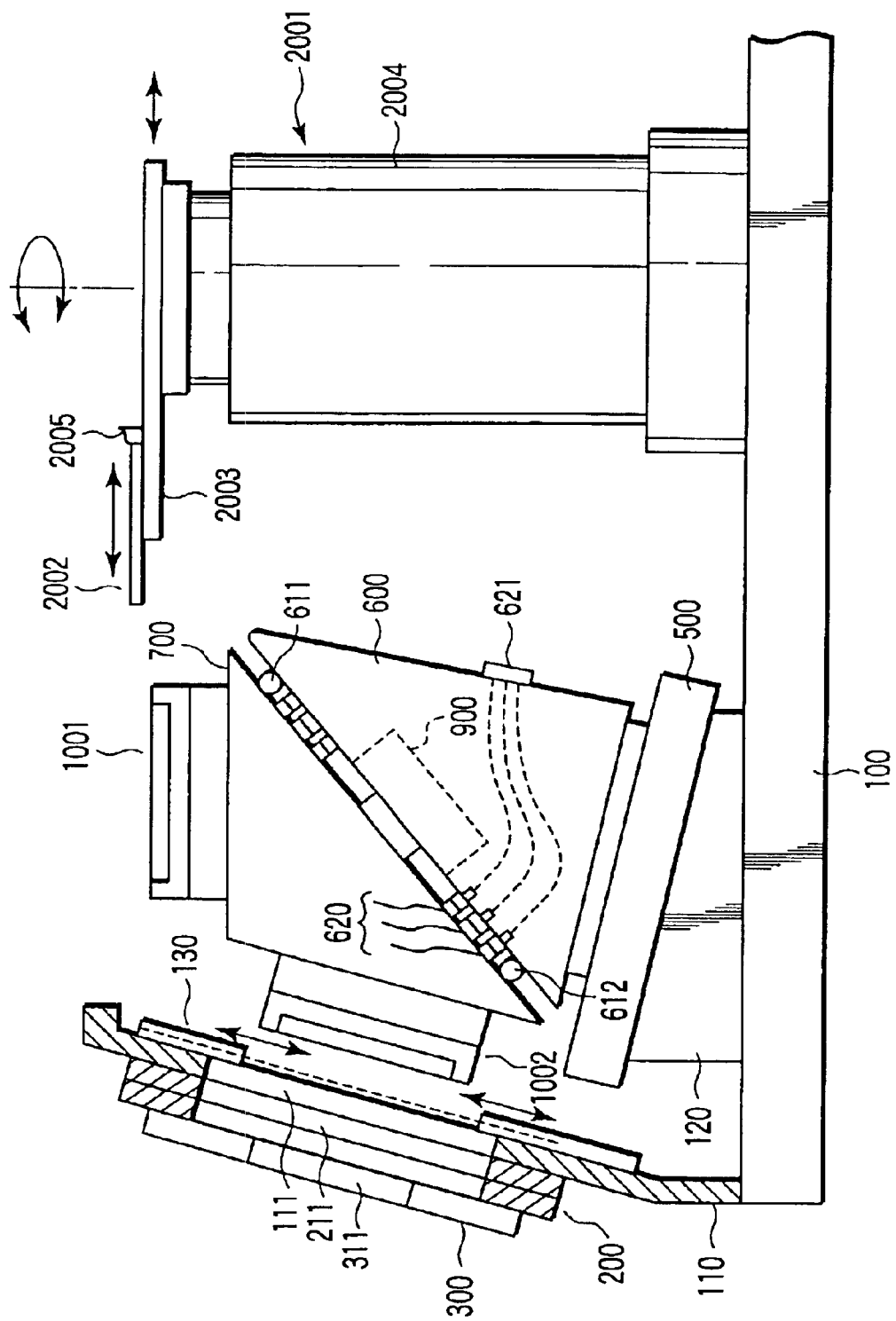
FIG. 8 is an explanatory diagram showing the structure of an apparatus according to still another embodiment of the present invention.

FIG. 8 schematically shows a panel supply device 2001 for supplying display panels alternately to the pallet devices 1001 and 1002. The panel supply device 2001 transfers a display panel 2002 by means of a slide arm 2003. The slide arm 2003 is horizontally rotated by a rotary drive device 2004. In a position different from that shown in FIG. 8, the slide arm 2003 receives the display panel 2002 from an external device, and rotates. Then, it transfers the display panel 2002 to the pallet device 1001 by sliding. When the display panel 2002 comes to a predetermined position beside the pallet device 1001, it is pushed out by a pushing pin 2005, and mounted on the panel device 1001. In this state, the panel device 1001 attracts the display panel by the suction mechanism.

The display panel on the pallet 1001, which has been inspected, is attracted by a suction device (not shown) and transferred to a classifying mechanism.

Figure 9:
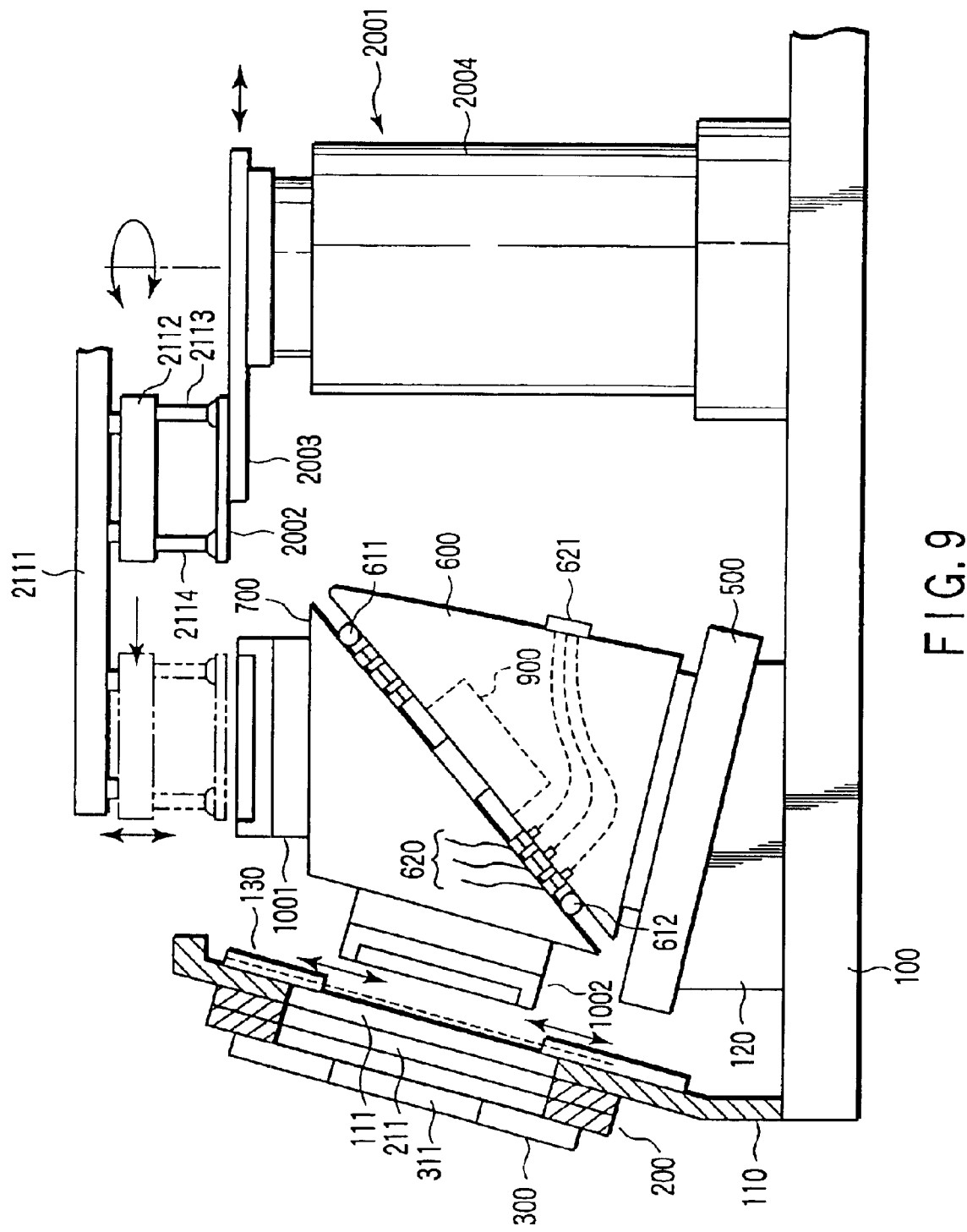
FIG. 9 is an explanatory diagram showing the structure of an apparatus according to a further embodiment of the present invention.

FIG. 9 shows still another embodiment of the present invention. It shows a transfer device for transferring a display panel without a sliding mechanism. The transfer device has a transfer movement unit 2112 attached under a rail 2111. The transfer movement unit 2112 has suction legs 2113 and 2114. It can attract the display panel 2002 by suction at the distal ends of the suction legs 2113 and 2114. The transfer movement unit 2112 transfers the display panel to a position above the pallet device 1001, slightly lowers it, and relieves the suction force. As a result, the display panel can be placed on the pallet device.

Figure 10:
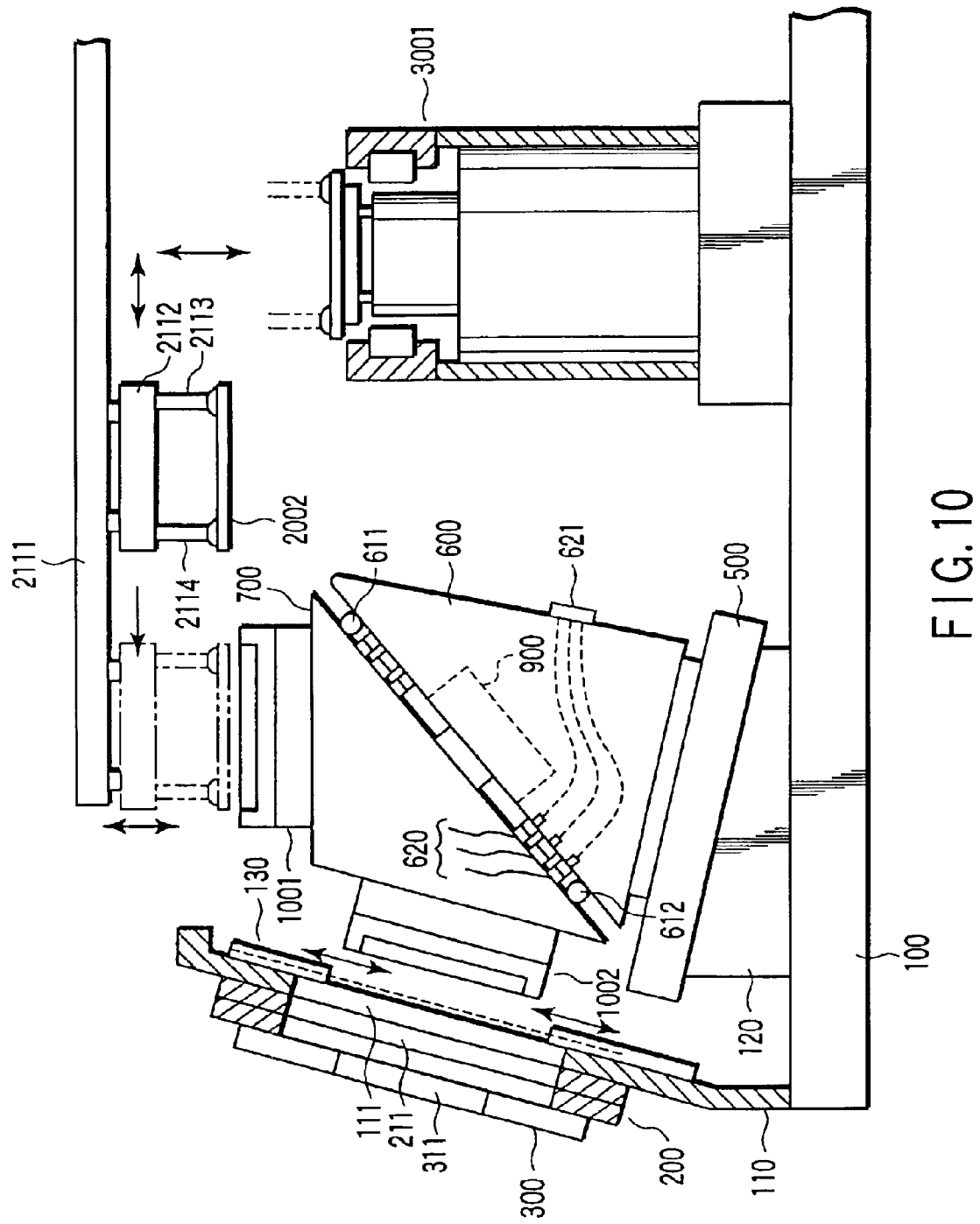
FIG. 10 is an explanatory diagram showing the structure of an apparatus according to a still further embodiment of the present invention.

FIG. 10 shows an example, in which a display panel is conveyed by a conveyor device 3001 and supplied to the pallet device by the transfer movement unit (shown in FIG. 9).

Figure 11:
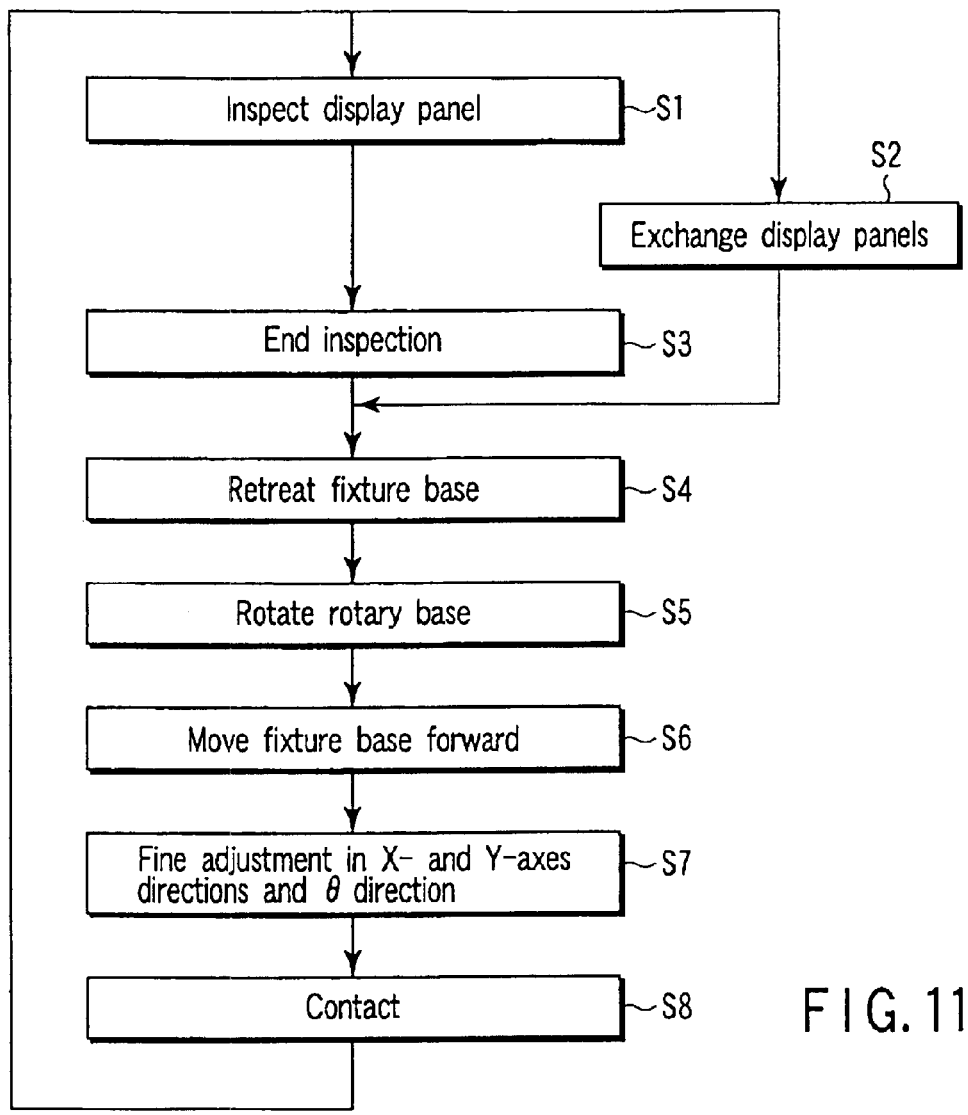
FIG. 11 is a flowchart for explaining basic operations of the apparatus of the present invention.

FIG. 11 is a flowchart for explaining basic operations of the apparatus of the present invention. While inspection of a display panel on the front surface of the rotary base is being carried out (steps S1 and S3), a display panel on the top surface thereof is exchanged with another panel (step S2). When the inspection is completed, the fixture base 600 is retracted by the Z-axis drive mechanism 500, so that the rotary base can be rotated safely in a sufficiently wide space (step S4). Then, the rotary base 700 is rotated to be set in a predetermined posture (step S5). Thereafter, the fixture base 600 is moved forward by the Z-axis drive mechanism 500. Thus, fine adjustment in X- and Y-axes and θ directions is performed, with the result that the display panel can be accurately positioned with respect to the probe unit (step S7). Then, the fixture base 600 is driven in the Z-axis direction. Thus, actual electrical contact is completed (step S8). Then, the operation returns to step S1.

Figure 12:
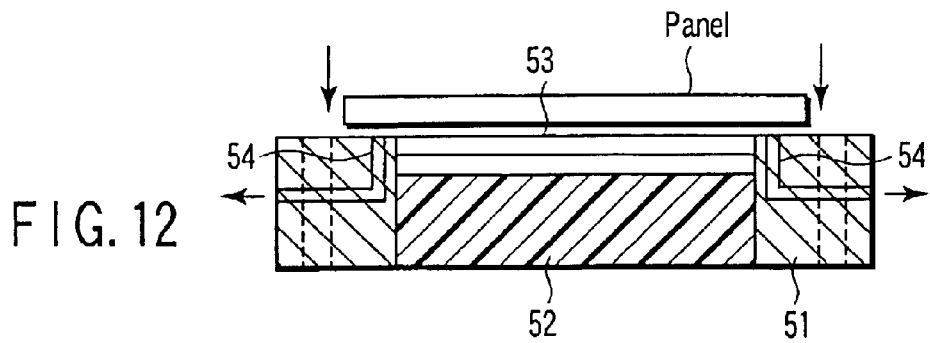
FIG. 12 is a diagram showing the structure of another example of the pallet device used in the apparatus of the present invention.

FIG. 12 shows another example of the pallet used in the pallet device 1001. A pallet 1305 has a frame 51 made of metal or resin, a transparent resin plate 52 fitted to the opening of the frame 51, and a diffusion plate (milky-white plate) 53 overlaid on the upper surface of the transparent resin plate 52. A plurality of L-shaped suction holes 54 are formed in the frame 51, so as to connect the upper and side surfaces of the frame. As a result, a panel can be attracted to the upper surface of the pallet 1305.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A display panel inspection apparatus comprising:
   a rotary base having first and second surfaces on which display panels are to be placed and a third surface which is a rotation surface, the rotary base having a substantially triangular cross section including first, second and third sides in a side view, the first and second sides corresponding to sides of the first and second surfaces, the third side corresponding to a side of the third surface, and a rotation shaft being set in a substantially central portion of the third surface and perpendicular to the third surface;
   a fixture base which has a driving section that rotates the rotation shaft and an opposing surface opposing to the third surface, and which supports the rotary base to be rotatable about the rotation shaft;
   a Z-axis drive mechanism which supports the fixture base and moves the fixture base frontward and backward in a state where the opposing side of the fixture base faces frontward; and
   a probe unit which faces in proximity to one surface of the rotary base when the fixture base is moved forward to a predetermined position by the Z-axis drive mechanism.

2. The display panel inspection apparatus according to claim 1, wherein the first surface of the rotary base is horizontal, the second surface thereof faces the probe unit, and when the second surface of the rotary base is horizontal, the first surface thereof faces the probe unit.

3. A display panel inspection method comprising:
   providing a display panel inspection apparatus including a rotary base having first and second surfaces on which display panels are to be placed and a third surface which is a rotation surface, the rotary base having a substantially triangular cross section including first, second and third sides in a side view, the first and second sides corresponding to sides of the first and second surfaces, the third side corresponding to a side of the third surface, and a rotation shaft being set in a substantially central portion of the third surface and perpendicular to the third surface; a fixture base which has a driving section that rotates the rotary shaft and an opposing surface opposing to the third surface and which supports the rotary base to be rotatable about the rotation shaft; a Z-axis drive mechanism which supports the fixture base and moves the fixture base frontward and backward in a state where the opposing side of the fixture base faces frontward; and a probe unit which faces in proximity to one surface of the rotary base when the fixture base is moved forward to a predetermined position by the Z-axis drive mechanism;
   inspecting a first display panel on the first surface of the rotary base by the probe unit;
   during the inspection of the first display panel, exchanging a third display panel on the second surface of the rotary base, which has been inspected, with a second display panel to be inspected next;
   after completion of inspecting the first display panel, retreating the fixed base by the Z-axis drive mechanism; and
   rotating the rotary base to inspect the second display panel.

4. A display panel inspection apparatus comprising:
   a rotary base having first and second surfaces on which display panels are to be placed and a third surface which is a rotation surface, the rotary base having a substantially triangular cross section including first, second and third sides in a side view, the first and second sides corresponding to sides of the first and second surfaces, the third side corresponding to a side of the third surface, and a rotation shaft being set in a substantially central portion of the third surface and perpendicular to the third surface;
   a fixture base which has a driving section that rotates the rotation shaft and an opposing surface opposing to the third surface, and which supports the rotary base to be rotatable about the rotation shaft;
   a Z-axis drive mechanism which supports the fixture base and moves the fixture base frontward and backward in a state where the opposing side of the fixture base faces frontward;
   a probe unit which faces in proximity to one surface of the rotary base when the fixture base is moved forward to a predetermined position by the Z-axis drive mechanism; and
   an X-, Y-, and θ axes adjustment stage device which controls the positioning between the probe unit and a display panel subject to inspection.

5. The display panel inspection apparatus according to claim 2, further comprising pallet devices, which are provided on the first and second surfaces and support the display panels, each of the pallet devices having a backlight.

6. The display panel inspection apparatus according to claim 2, further comprising a front panel having a window and a stage device attached to surround the window of the front panel.

* * * * *